(12) United States Patent
Jenkins et al.

(10) Patent No.: US 7,104,990 B2
(45) Date of Patent: Sep. 12, 2006

(54) LOOP STRUCTURE INCLUDING INFLATABLE THERAPEUTIC DEVICE

(75) Inventors: Thomas R. Jenkins, Oakland, CA (US); Jeffrey S. Jones, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 338 days.

(21) Appl. No.: 10/721,804

(22) Filed: Nov. 24, 2003

(65) Prior Publication Data

US 2004/0106920 A1    Jun. 3, 2004

Related U.S. Application Data

(62) Division of application No. 09/730,010, filed on Dec. 4, 2000.

(51) Int. Cl.
*A61B 18/18* (2006.01)

(52) U.S. Cl. .......................................... 606/49; 606/41

(58) Field of Classification Search ................ 606/41, 606/45–50, 192–194; 607/101–105
See application file for complete search history.

(56) References Cited

U.S. PATENT DOCUMENTS

| | | |
|---|---|---|
| 1,207,479 A | 12/1916 | Bisgaard |
| 4,033,331 A | 7/1977 | Guss et al. |
| 4,181,131 A | 1/1980 | Ogiu |
| 4,245,624 A | 1/1981 | Komiya |
| 4,983,165 A | 1/1991 | Loiterman |
| 5,002,532 A | 3/1991 | Gaiser |
| 5,041,085 A | 8/1991 | Osbourne |
| 5,098,412 A | 3/1992 | Shiu |
| 5,102,416 A | 4/1992 | Rock |
| 5,156,151 A | 10/1992 | Imran |
| 5,213,576 A | 5/1993 | Abiuso |
| 5,263,493 A | 11/1993 | Avitall |
| 5,306,245 A | 4/1994 | Heaven |
| 5,368,567 A | 11/1994 | Lee |
| 5,368,592 A | 11/1994 | Stern |
| 5,370,675 A | 12/1994 | Edwards |
| 5,380,319 A | 1/1995 | Saito |
| 5,399,165 A | 3/1995 | Paul, Jr. |
| 5,415,656 A | 5/1995 | Tihon et al. |
| 5,437,665 A | 8/1995 | Munro |
| 5,439,006 A | 8/1995 | Brennen |
| 5,482,037 A | 1/1996 | Borghi |
| 5,487,385 A | 1/1996 | Avitall |
| 5,499,971 A | 3/1996 | Shapland |
| 5,505,730 A | 4/1996 | Edwards |
| 5,549,661 A | 8/1996 | Kordis |

(Continued)

FOREIGN PATENT DOCUMENTS

DE    3920707 A1    1/1991

(Continued)

OTHER PUBLICATIONS

Claim as Apr. 2, 2004 in U.S. Appl. No. 10/213,031, filed Aug. 5, 2005 and published as U.S. Pub. App. No. 20030014037 A1.

*Primary Examiner*—Michael Peffley
(74) *Attorney, Agent, or Firm*—Henricks, Slavin & Holmes LLP (57) ABSTRACT

A probe including an elongate body defining a distal region adapted to be bent into a loop and an inflatable tissue coagulation body supported on the elongate body distal region.

21 Claims, 6 Drawing Sheets

U.S. PATENT DOCUMENTS

| | | | |
|---|---|---|---|
| 5,571,088 A | 11/1996 | Lennox | |
| 5,582,609 A | 12/1996 | Swanson | |
| 5,637,090 A | 6/1997 | McGee | |
| 5,672,174 A | 9/1997 | Gough | |
| 5,702,368 A | 12/1997 | Stevens | |
| 5,702,438 A | 12/1997 | Avitall | |
| 5,709,224 A | 1/1998 | Behl | |
| 5,730,127 A | 3/1998 | Avitall | |
| 5,738,683 A | 4/1998 | Osypka | |
| 5,782,899 A | 7/1998 | Imran | |
| 5,800,482 A | 9/1998 | Pomeranz | |
| 5,800,484 A | 9/1998 | Gough | |
| 5,820,591 A | 10/1998 | Thompson | |
| 5,830,213 A | 11/1998 | Panescu | |
| 5,836,947 A | 11/1998 | Fleischman | |
| 5,860,974 A | 1/1999 | Abele | |
| 5,863,291 A | 1/1999 | Schaer | |
| 5,879,295 A | 3/1999 | Li | |
| 5,895,417 A * | 4/1999 | Pomeranz et al. | 607/101 |
| 5,910,129 A | 6/1999 | Koblish | |
| 5,938,660 A | 8/1999 | Swartz | |
| 5,961,513 A | 10/1999 | Swanson | |
| 5,967,984 A | 10/1999 | Chu | |
| 5,971,983 A | 10/1999 | Lesh | |
| 6,012,457 A * | 1/2000 | Lesh | 128/898 |
| 6,016,811 A | 1/2000 | Knopp | |
| 6,029,671 A | 2/2000 | Stevens | |
| 6,048,329 A | 4/2000 | Thompson | |
| 6,053,913 A * | 4/2000 | Tu et al. | 606/41 |
| 6,064,902 A | 5/2000 | Haissaguerre | |
| 6,071,274 A | 6/2000 | Thompson | |
| 6,071,279 A | 6/2000 | Whayne | |
| 6,071,281 A | 6/2000 | Burnside | |
| 6,076,012 A * | 6/2000 | Swanson et al. | 604/21 |
| 6,086,581 A | 7/2000 | Reynolds | |
| 6,120,500 A | 9/2000 | Bednarek | |
| 6,161,543 A | 12/2000 | Cox | |
| 6,179,835 B1 | 1/2001 | Panescu | |
| 6,203,525 B1 | 3/2001 | Whayne | |
| 6,217,528 B1 | 4/2001 | Koblish | |
| 6,237,605 B1 | 5/2001 | Vaska | |
| 6,251,093 B1 | 6/2001 | Valley | |
| 6,306,133 B1 | 10/2001 | Tu et al. | |
| 6,311,692 B1 | 11/2001 | Vaska | |
| 6,314,962 B1 | 11/2001 | Vaska | |
| 6,314,963 B1 | 11/2001 | Vaska | |
| 6,332,880 B1 | 12/2001 | Yang | |
| 6,402,746 B1 | 6/2002 | Whayne | |
| 6,413,234 B1 | 7/2002 | Thompson | |
| 6,454,758 B1 | 9/2002 | Thompson | |
| 6,454,766 B1 | 9/2002 | Swanson | |
| 6,464,700 B1 | 10/2002 | Koblish | |
| 6,485,489 B1 | 11/2002 | Teirstein et al. | |
| 6,527,769 B1 * | 3/2003 | Langberg et al. | 606/41 |
| 6,529,756 B1 | 3/2003 | Phan | |
| 6,542,781 B1 | 4/2003 | Koblish | |
| 6,607,505 B1 | 8/2003 | Thompson | |
| 6,613,046 B1 | 9/2003 | Jenkins | |
| 6,645,199 B1 | 11/2003 | Jenkins | |
| 6,666,858 B1 * | 12/2003 | Lafontaine | 606/21 |
| 6,904,303 B1 | 6/2005 | Phan et al. | |
| 6,904,464 B1 | 6/2005 | Van Langen et al. | |
| 7,025,766 B1 | 4/2006 | Whayne et al. | |
| 7,029,471 B1 | 4/2006 | Thompson et al. | |
| 2003/0014037 A1 | 1/2003 | Thompson | |
| 2003/0069570 A1 | 4/2003 | Witzel et al. | |

FOREIGN PATENT DOCUMENTS

| | | |
|---|---|---|
| EP | 0238106 A1 | 9/1987 |
| EP | 0737487 A2 | 10/1996 |
| EP | 0868922 A2 | 10/1998 |
| EP | 0916360 A2 | 5/1999 |
| EP | 1042990 A1 | 10/2000 |
| WO | WO-95/10253 A1 | 4/1995 |
| WO | WO-98/26724 A1 | 6/1998 |
| WO | WO-99/02096 A1 | 1/1999 |

* cited by examiner

LOOP STRUCTURE INCLUDING INFLATABLE THERAPEUTIC DEVICE

CROSS-REFERENCE TO RELATED APPLICATIONS

This application is a divisional of co-pending U.S. application Ser. No. 09/730,010, filed Dec. 4, 2000.

BACKGROUND OF THE INVENTIONS

1. Field of Inventions

The present inventions relate generally to medical devices that support therapeutic elements in contact with body tissue and, more particularly, to loop structures that support therapeutic elements in contact with bodily tissue.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive.

Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

Catheters used to create lesions typically include a relatively long and relatively flexible body portion that has a soft tissue coagulation electrode on its distal end and/or a series of spaced tissue coagulation electrodes near the distal end. The portion of the catheter body portion that is inserted into the patient is typically from 23 to 55 inches in length and there may be another 8 to 15 inches, including a handle, outside the patient. The length and flexibility of the catheter body allow the catheter to be inserted into a main vein or artery (typically the femoral artery), directed into the interior of the heart, and then manipulated such that the coagulation electrode contacts the tissue that is to be ablated. Fluoroscopic imaging is used to provide the physician with a visual indication of the location of the catheter.

In some instances, the proximal end of the catheter body is connected to a handle that includes steering controls. Exemplary catheters of this type are disclosed in U.S. Pat. No. 5,582,609. In other instances, the catheter body is inserted into the patient through a sheath and the distal portion of the catheter is bent into loop that extends outwardly from the sheath. This may be accomplished by pivotably securing the distal end of the catheter to the distal end of the sheath, as is illustrated U.S. Pat. No. 6,071,279. The loop is formed as the catheter is pushed in the distal direction. The loop may also be formed by securing a pull wire to the distal end of the catheter that extends back through the sheath, as is illustrated in U.S. Pat. No. 6,048,329. Loop catheters are advantageous in that they tend to conform to different tissue contours and geometries and provide intimate contact between the spaced tissue coagulation electrodes (or other diagnostic or therapeutic elements) and the tissue.

One lesion that has proven to be difficult to form with conventional catheters are lesions that are used to isolate the pulmonary vein and cure ectopic atrial fibrillation. Lesions may be formed within the pulmonary vein itself or in the tissue surrounding the pulmonary vein (the "pulmonary vein ostium") to isolate the pulmonary vein. Conventional steerable catheters and loop catheters have proven to be less than effective with respect to the formation of such circumferential lesions. For example, it can be difficult to achieve the level of tissue contact required to form an effective lesion.

A variety of inflatable lesion formation structures have also been proposed. Depending on their size, such structures are typically inflated within the pulmonary vein or inflated and then advanced into contact with the pulmonary vein ostium. Such devices tend to establish better tissue contact than conventional steerable catheters and loop catheters. However, they also act as a plug and occlude the flow of blood through the pulmonary vein. In addition, the inventors herein have determined that it can be difficult to manufacture a balloon that will be large enough when inflated to engage the entire circumference of the pulmonary vein ostium, and small enough when deflated to be advanced through a sheath to the ostium.

Accordingly, the inventors herein have determined that a need exists for structures that can be used to create effective lesions within or around the pulmonary vein without occluding blood flow.

SUMMARY OF THE INVENTION

Accordingly, the general object of the present inventions is to provide a device that avoids, for practical purposes, the aforementioned problems. In particular, one object of the present inventions is to provide a device that can be used to create lesions in or around the pulmonary vein and other bodily orifices in a more effective manner than conventional apparatus. Another object of the present invention is to provide a device that can be used to create lesions in or around the pulmonary vein and other bodily orifices with occluding the flow of blood or other body fluids. Still another object of the present invention is to provide a device including an inflatable structure that can be used to create lesions in or around the pulmonary vein and is also small enough when deflated to be advanced through a sheath.

In order to accomplish some of these and other objectives, a probe in accordance with one embodiment of a present invention includes an elongate body defining a distal region adapted to be bent into a loop and an inflatable tissue coagulation body supported on the elongate body distal region. In a preferred implementation, the inflatable tissue coagulation body will be a half-balloon structure located on one side of the loop and spaced inwardly from the apex (or distal end) of the loop.

The present probe provides a number of advantages over conventional catheter devices. For example, the present probe provides superior tissue contact at the pulmonary vein ostium. The apex (or distal end) of the loop in the present probe may be inserted into the pulmonary vein to such an extent that the inflatable tissue coagulation body will be adjacent to the pulmonary vein ostium. Such positioning will wedge the inflatable tissue coagulation body into close contact with the ostium and, when the tissue coagulation body is inflated, the level of contact will be increased. After the lesion has been formed, the tissue coagulation body may be deflated and the loop repositioned so that another lesion can be formed. This process will continue until a continuous circumferential lesion has been formed around the ostium.

When the apex of the present probe is inserted into the pulmonary vein ostium, the present probe defines an open region that allows blood to pass therethrough. As a result, the present probe facilitates the formation of a circumferential lesion without the occlusion of blood associated with conventional inflatable lesion formation structures.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Exemplary Catheter and Expandable Lesion Formation Device Structures
III. Exemplary Loop Formation Devices
IV. Methods of Use The section titles and overall organization of the present detailed description are for the purpose of convenience only and are not intended to limit the present inventions.

I. Introduction

The present inventions may be used within body lumens, chambers or cavities for diagnostic or therapeutic purposes in those instance where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, uterus, and other regions of the body.

With regard to the treatment of conditions within the heart, the present inventions are designed to produce intimate tissue contact with target substrates associated with various arrhythmias, namely atrial fibrillation, atrial flutter, and ventricular tachycardia. For example, the distal portion of a catheter in accordance with a present invention, which may include diagnostic and/or soft tissue coagulation electrodes, can be used to create lesions within or around the pulmonary vein to treat ectopic atrial fibrillation.

The structures are also adaptable for use with probes other than catheter-based probes. For example, the structures disclosed herein may be used in conjunction with hand held surgical devices (or "surgical probes"). The distal end of a surgical probe may be placed directly in contact with the targeted tissue area by a physician during a surgical procedure, such as open heart surgery. Here, access may be obtained by way of a thoracotomy, median sternotomy, or thoracostomy. Exemplary surgical probes are disclosed in U.S. Pat. No. 6,071,281, which is incorporated herein by reference.

Surgical probe devices in accordance with the present inventions preferably include a handle, a relatively short shaft, and one of the distal assemblies described hereafter in the catheter context. Preferably, the length of the shaft is about 4 inches to about 18 inches. This is relatively short in comparison to the portion of a catheter body that is inserted into the patient (typically from 23 to 55 inches in length) and the additional body portion that remains outside the patient. The shaft is also relatively stiff. In other words, the shaft is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

II. Exemplary Catheter and Expandable Lesion Formation Device Structures

Figures 8, 9, 10, 11:
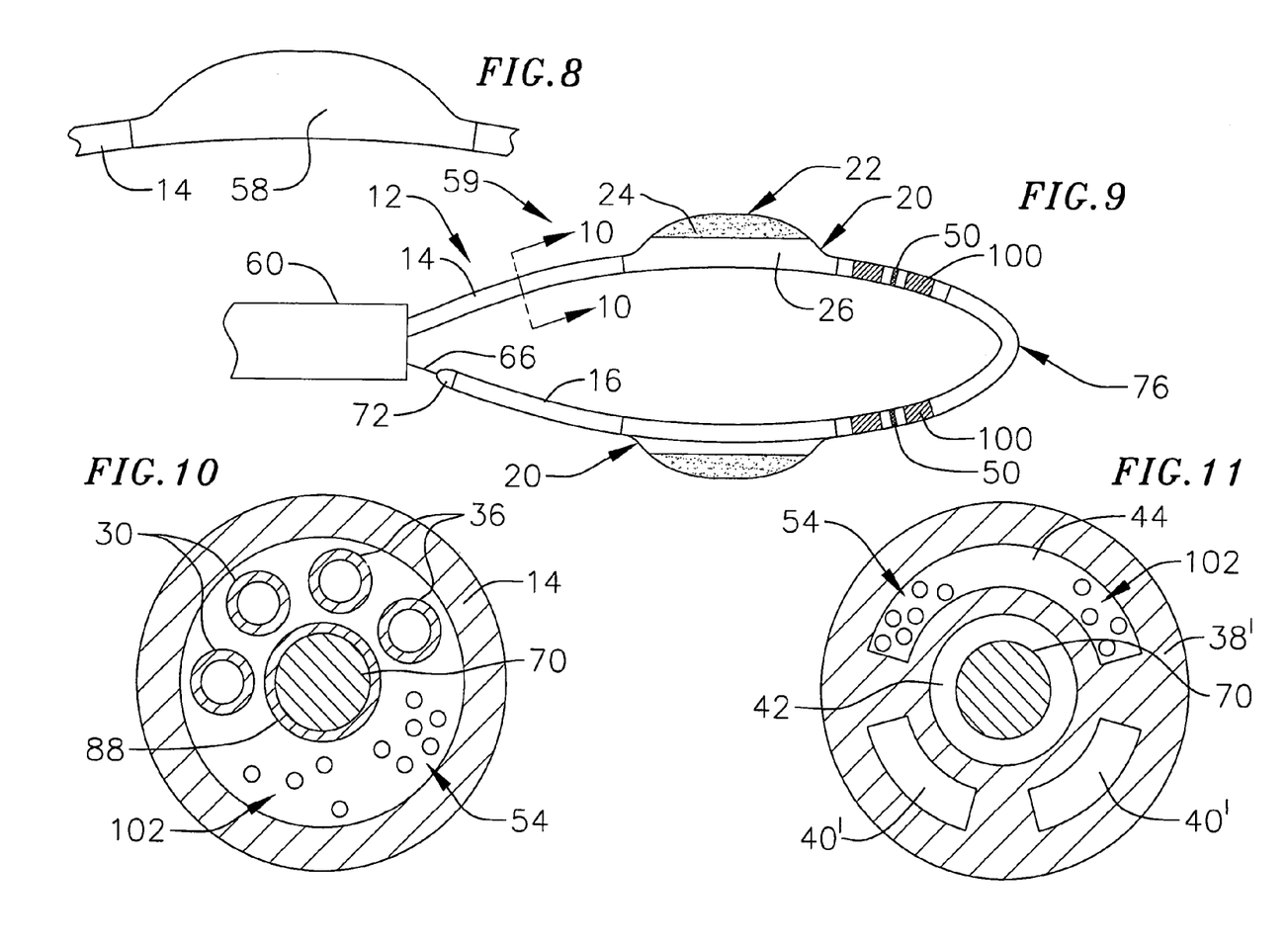
FIG. 8 is a side view of an expandable tissue heating structure in accordance with another preferred embodiment of a present invention.
FIG. 9 is a side view of the distal portion of a catheter-based probe in accordance with another preferred embodiment of a present invention.
FIG. 10 is a section view taken along line 10—10 in FIG. 9.
FIG. 11 is a section view in accordance with another preferred embodiment of a present invention.

As illustrated for example in FIGS. 1–6, a catheter 10 in accordance with a preferred embodiment of a present invention includes a flexible catheter body 12 that may be formed from a biocompatible thermoplastic material such as braided or unbraided Pebax® (polyether block emide), polyethylene, or polyurethane, and is preferably about 5 French to about 9 French in diameter. Preferably, the catheter body 12 will have a two part construction consisting of a relatively long less flexible proximal member 14 (formed from braided Pebax®) and a relatively short flexible distal member 16 (formed from unbraided Pebax®). The proximal and distal members 14 and 16 may be bonded together with an overlapping thermal bond or adhesive bonded together end to end over a sleeve in what is referred to as a "butt bond." The proximal end of the catheter body 12 is secured to a handle 18. An expandable (and collapsible) coagulation body is mounted on the proximal member 14. As described below, the expandable coagulation body may be either an expandable porous electrode structure 20 (as shown in FIGS. 1–5) or an expandable structure 58 that can be heated to a predetermined temperature (as shown in FIG. 8).

The exemplary expandable porous electrode 20, which is formed from an electrically non-conductive thermoplastic or elastomeric material, includes a porous region 22 having micropores 24 and a non-porous region 26. Liquid pressure is used to inflate the expandable porous electrode 20 and maintain it in its expanded state. The liquid used to fill the expandable porous electrode 20 is an electrically conductive liquid that establishes an electrically conductive path to convey RF energy from the electrode 20 to tissue.

Figure 5:
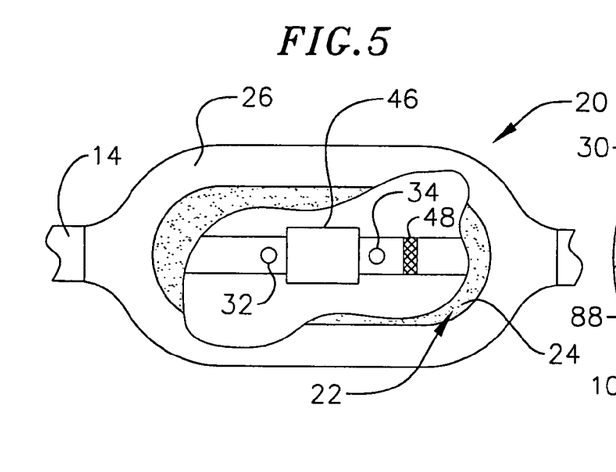
FIG. 5 is a top cutaway view of the distal portion of the probe illustrated in FIG. 1.
Figures 6, 7:
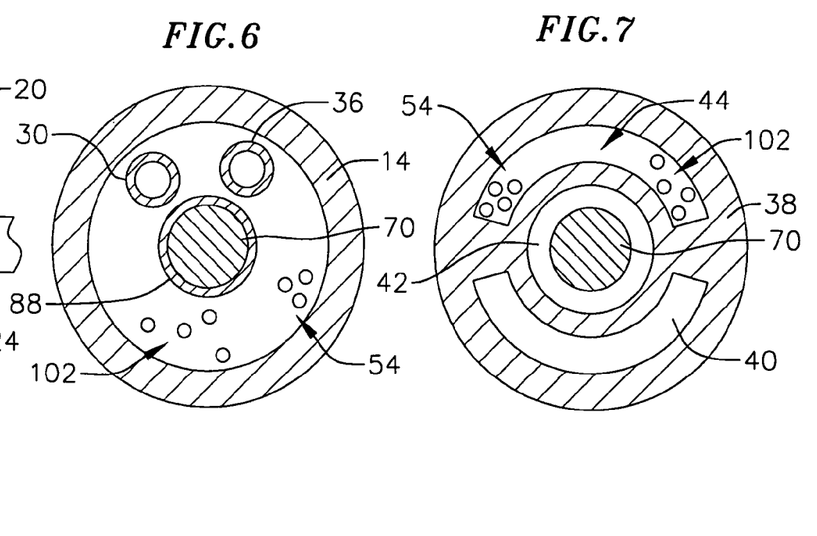
FIG. 6 is a section view taken along line 6—6 in FIG. 4.
FIG. 7 is a section view in accordance with another preferred embodiment of a present invention.

Referring more specifically to FIGS. 5 and 6, the conductive liquid is supplied under pressure to the expandable porous electrode 20 by way of an infusion/ventilation port 28 in the handle 18, an inlet lumen 30 that is connected to the port, and an aperture 32 formed in the catheter body 12. The inlet lumen extends 30 from the port 28 to the aperture 32. The pressure should be relatively low (less than 5 psi) and will vary in accordance with the desired level of inflation, strength of materials used and the desired degree of body flexibility. The expandable porous electrode 20 will then expand from its collapsed, low profile state (between about 2 mm and about 4 mm in diameter) to its expanded state (between about 5 mm and about 15 mm in diameter). [Use of the term "diameter" is not intended to imply that the electrode 20 is necessarily circular in cross-section.] The liquid is removed by way of the aperture 34, which is connected to an outlet lumen 36 that is also connected to the infusion/ventilation port 28. Preferably, a vacuum force is applied to the outlet lumen 36 at the infusion/ventilation port 28 to remove the liquid.

Alternatively, as illustrated for example in FIG. 7, the proximal member 14 may replaced by a proximal member 38 that is a multi-lumen extrusion with lumens 40, 42 and 44. Lumen 40, which is connected to the infusion/ventilation port 28 in the handle 18, functions as both an inlet lumen and an outlet. The aperture 32 (FIG. 5) is connected to the lumen 40 and aperture 34 may be eliminated. The distal end of the lumen 40 is sealed with an appropriate plug (not shown). Liquid may be supplied to the lumen 40 under pressure and withdrawn by applying a vacuum force at the infusion/ventilation port 28.

It is preferable, although not required, that the expandable porous electrode 20 be placed proximally of the loop apex 76 (discussed below) regardless of the type of fluid lumen employed because the lumens could be pinched, and flow disrupted, at the apex.

Although the shape may be varied to suit particular applications, the preferred geometry of the expandable porous electrode 20 is essentially that of an elongate half-balloon. In other words, when expanded, the electrode 20 extends radially outwardly away from the loop 62 (discussed below) in the manner illustrated for example in FIGS. 1–3. The length of the exemplary electrode 20 is about 1.0 cm, but may range from 0.5 cm to 2.0 cm, while the width is about 5 mm, but may range from 3 mm to 15 mm. The length of the exemplary porous region 22 is about 3 mm, but may range from 2 mm to 5 mm, while the width is about 1.5 mm, but may range from 0.5 mm to 3 mm. This porous electrode configuration is especially useful for forming relatively deep lesions in the entrance to the pulmonary vein.

As illustrated for example in FIG. 5, an electrode 46 formed from material with both relatively high electrical conductivity and relatively high thermal conductivity is carried within the expandable porous electrode 20. Suitable materials include gold, platinum, and platinum/iridium. Noble metals are preferred. The pores 24 establish ionic transport of the tissue coagulating energy from the electrode 46 through the electrically conductive fluid to tissue outside the porous electrode 20. The liquid preferably possesses a low resistivity to decrease ohmic loses, and thus ohmic heating effects, within the porous electrode 20. The composition of the electrically conductive liquid can vary. A hypertonic saline solution, having a sodium chloride concentration at or near saturation, which is about 20% weight by volume is preferred. Hypertonic saline solution has a low resistivity of only about 5 ohm∘cm, compared to blood resistivity of about 150 ohm∘cm and myocardial tissue resistivity of about 500 ohm·cm. Alternatively, the fluid can be a hypertonic potassium chloride solution. This medium, while promoting the desired ionic transfer, requires closer monitoring of the rate at which ionic transport occurs through the pores 24, to prevent potassium overload. When hypertonic potassium chloride solution is used, it is preferred keep the ionic transport rate below about 1 mEq/min.

Ionic contrast solution, which has an inherently low resistivity, can be mixed with the hypertonic sodium or potassium chloride solution. The mixture enables radiographic identification of the porous electrode 20 without diminishing the ionic transfer through the pores 24.

Due largely to mass concentration differentials across the pores 24, ions in the conductive fluid will pass into the pores because of concentration differential-driven diffusion. Ion diffusion through the pores 24 will continue as long as a concentration gradient is maintained across the porous electrode 20. The ions contained in the pores 24 provide the means to conduct current across the porous electrode 20. When RF energy is conveyed from a RF power supply and control apparatus to the electrode 46, electric current is carried by the ions within the pores 24. The RF currents provided by the ions result in no net diffusion of ions, as would occur if a DC voltage were applied, although the ions do move slightly back and forth during the RF frequency application. This ionic movement (and current flow) in response to the applied RF field does not require perfusion of liquid through the pores 24. The ions convey RF energy through the pores 24 into tissue to a return electrode, which is typically an external patch electrode (forming a unipolar arrangement). Alternatively, the transmitted energy can pass through tissue to an adjacent electrode (forming a bipolar arrangement). The RF energy heats tissue (mostly ohmically) to coagulate the tissue and form a lesion.

Figures 1, 2, 3:
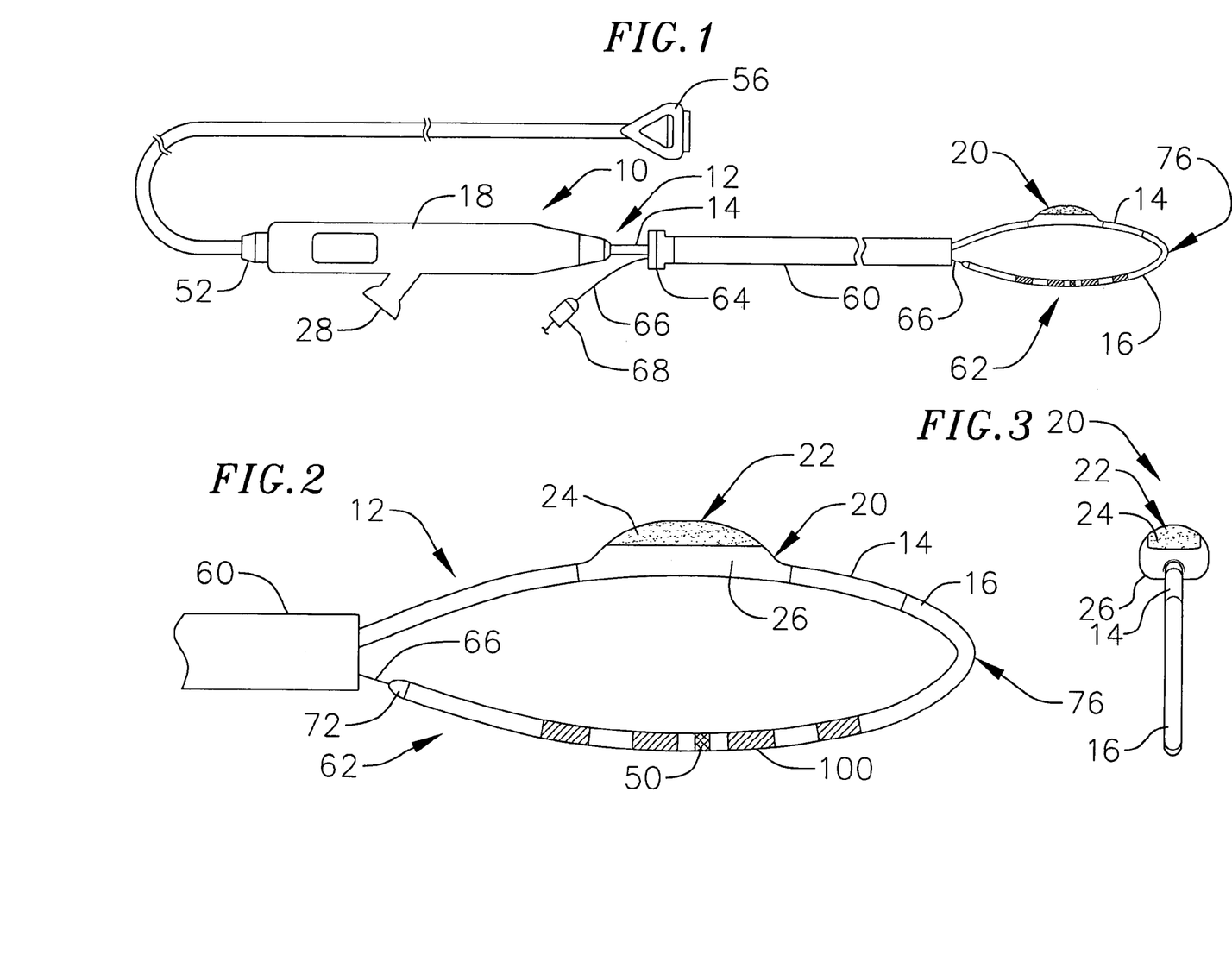
FIG. 1 is a side view of a catheter-based probe in accordance with a preferred embodiment of a present invention.
FIG. 2 is an enlarged view of the distal portion of the probe illustrated in FIG. 1.
FIG. 3 is an end view of the distal portion of the probe illustrated in FIG. 1.
Figure 4:
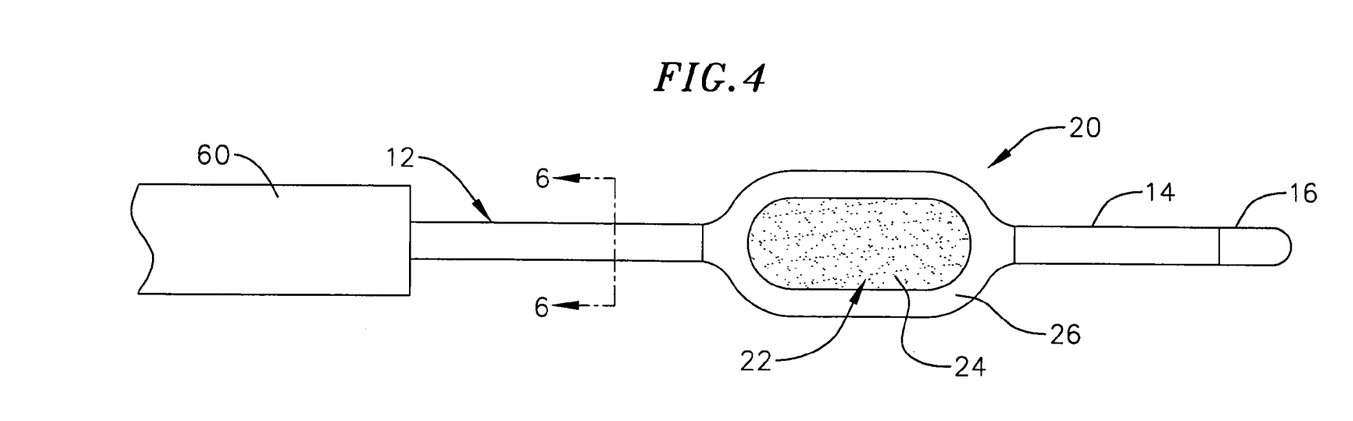
FIG. 4 is a top view of the distal portion of the probe illustrated in FIG. 1.

The temperature of the fluid is preferably monitored for power control purposes. To that end, a temperature sensing element, such as the illustrated thermocouple 48, may mounted on the catheter body 12 within the expandable porous electrode 20. A reference thermocouple 50 (FIG. 2) may be positioned on the distal member 16. Alternatively, a thermistor or other temperature sensing element within the electrode 20 may be used in place of the thermocouple and reference thermocouple arrangement. Referring to FIGS. 1 and 6, the electrode 46, thermocouple 48 and reference thermocouple 50 are respectively connected to an electrical connector 52 by electrical conductors 54 which extend through the catheter body. The catheter 10 may be connected to a suitable RF power supply and control apparatus by a connector 56. Additional information concerning controllers which control power to electrodes based on a sensed temperature is disclosed in U.S. Pat. Nos. 5,456,682, 5,582,609 and 5,755,715.

With respect to materials, the porous region 22 of the expandable porous electrode 20 is preferably formed from regenerated cellulose or a microporous elastic polymer. Materials such as nylons (with a softening temperature above 100° C.), PTFE, PEI and PEEK that have micropores created through the use of lasers, electrostatic discharge, ion beam bombardment or other processes may also be used. Such materials would preferably include a hydrophilic coating. The micropores should be about 1 to 5 μm in diameter and occupy about 1% of the surface area of the porous region 22. A slightly larger pore diameter may be employed. Because the larger pore diameter would result in significant fluid transfer through the porous region, a saline solution having a sodium chloride concentration of about 0.9% weight by volume is preferred.

The non-porous regions are preferably formed from relatively elastic materials such as silicone and polyisoprene. However, other less elastic materials, such as Nylon®, Pebax®, polyethylene, polyesterurethane and polyester, may also be used. Here, the expandable porous electrode 20 may be provided with creased regions that facilitate the collapse of the porous electrode. A hydrophilic coating may be applied to the non-porous regions to facilitate movement of the porous electrode 20 in to and out of a sheath.

Additional information and examples of expandable and collapsible bodies are disclosed in U.S. patent application Ser. No. 08/984,414, entitled "Devices and Methods for Creating Lesions in Endocardial and Surrounding Tissue to Isolate Arrhythmia Substrates," U.S. Pat. No. 5,368,591, and U.S. Pat. No. 5,961,513, each of which is incorporated herein by reference.

Turning to FIG. 8, catheters in accordance with other embodiments of the present inventions may include a heated expandable (and collapsible) coagulation body 58 in place of the porous electrode 20. The exemplary coagulation body 58, which is bonded to and disposed around the proximal member 14, can be inflated with water, hypertonic saline solution, or other biocompatible fluids. The fluid may be supplied under pressure to the coagulation body 58, and withdrawn therefrom, through the infusion/ventilation port 28 in either of the manner described above with reference to FIGS. 6 and 7. Here too, the pressure should be relatively low (less than 5 psi) and will vary in accordance with the desired level of inflation, strength of materials used and the desired degree of body flexibility.

A fluid heating element is located within the expandable coagulation body 58. The fluid heating element is preferably an electrode (not shown) that may be formed from metals such as platinum, gold and stainless steel and mounted on the catheter body within the coagulation body 58. A bi-polar pair of electrodes may, alternatively, be used to transmit power through a conductive fluid, such as isotonic saline solution, to generate heat. The temperature of the fluid may be heated to about 90° C., thereby raising the temperature of the exterior of the expandable coagulation body 58 to approximately the same temperature for tissue coagulation. It should be noted, however, that the expandable coagulation body 58 tends to produce relatively superficial lesions.

Suitable materials for the exemplary expandable coagulation body 58 include relatively elastic thermally conductive biocompatible materials such as silicone and polyisoprene. Other less elastic materials, such as Nylon®, Pebax®, polyethylene and polyester, may also be used. Here, the expandable coagulation body will have to be formed with fold lines. Temperature sensing elements, such as the exemplary thermocouple 48 and reference thermocouple 50 illustrated in FIGS. 2 and 5, may also be provided. The heating electrode, thermocouple and reference thermocouple will be connected to the electrical connector 52 by electrical conductors which extend through the catheter body 12 in the manner described above.

Another exemplary embodiment, which is generally represented by reference numeral 59, is illustrated in FIGS. 9 and 10. The catheter 59 includes a pair of expandable porous electrode structures 20 that are either substantially identical to, or slight variations of, one another. The electrode structures 20 may be inflated together or separately. The expandable coagulation body 58 (FIG. 8) may be used in place of one or more of the electrode structures 20. With respect to infusion and ventilation, catheter 59 includes respective pairs of inlet lumens 30 and outlet lumens 36 that operate in the manner described above with reference to FIGS. 5 and 6.

Infusion and ventilation may, alternatively, be accomplished through the use of the proximal member 38' illustrated for example in FIG. 11. The proximal member 38' includes a pair of fluid lumens 40' that each function as an inlet and an outlet for a respective electrode structure 20. One of the lumens 40' is plugged to prevent fluid from flowing beyond the distal end of the proximal member 38'. A similarly configured distal member (not shown), with a single fluid lumen that is connected to the other lumen 40', is connected to the proximal member 38'. The distal end of this fluid lumen is also plugged. Liquid will be supplied to and withdrawn from each of the electrode structures 20 by way of the lumens in the manner described above with reference to FIG. 7.

In another exemplary embodiment, the catheter 59 may be configured such that the proximal electrode structure 20 is infused and ventilated in one of the manners described above with reference to FIGS. 6 and 7. The distal electrode structure 20, on the other hand, will be infused and ventilated through the use of the infusion/ventilation pull device 67 that is described below with reference to FIG. 15.

III. Exemplary Loop Formation Devices

As illustrated for example in FIGS. 1 and 2, the exemplary catheter 10 may be used in conjunction with a sheath 60 and configured such that the distal region of the catheter may be deployed in a loop 62. The sheath 60, which preferably has a greater inherent stiffness than the portion of the catheter body 12 that forms the loop 62, should be lubricious to reduce friction during movement of the catheter body. A handle 64, which is a Toughy Borst connector in the illustrated embodiment that can be used to fix the relative positions of the catheter body 12 and sheath 60, is mounted on the proximal end of the sheath. With respect to materials, the exemplary sheath 60 is a Pebax® and stainless steel braid composite. Other materials, such as polytetrafluoroethylene (PTFE), can also be used. The wall thickness of the sheath 60 is preferably about 0.013 inch, which will not add significantly to the overall thickness of the catheter body 12. Also, although the distal end of the sheath 60 is perpendicular to the longitudinal axis of the sheath in the exemplary embodiment, the distal end may also be cut at an angle and tapered in a transverse direction relative to the longitudinal axis of the sheath to effect the shape of the loop 62.

A pull wire 66 extends from the distal end of the catheter body 12 and through the sheath 60. The proximal end of the pull wire 66 includes an adjustable stop/handle 68. The pull wire 66 is preferably a flexible, inert cable constructed from strands of metal wire material, such as Nickel Titanium (commercially available under the trade name Nitinol®) or 17-7 stainless steel, that is about 0.012 to 0.018 inch in diameter. Alternatively, the pull wire 66 may be formed from a flexible, inert stranded or molded plastic material. The pull wire 66 is also preferably round in cross-section, although other cross-sectional configurations can be used.

Holding the pull wire 66 and handle 68 stationary, the physician deploys the loop 62 by advancing the catheter body 12 through the sheath 60. Once the loop 62 has been formed, the physician can pull on the pull wire 66 to decrease the exposed length of the pull wire beyond the distal end of the sheath 60. Further adjustments to the loop 62 may be made by advancing or retracting the catheter body 12 within the sheath 60 or by putting tension on the pull wire 66. The loop structure 60 may also be rotated by rotating the catheter body 12 with the handle 18.

Figure 12:
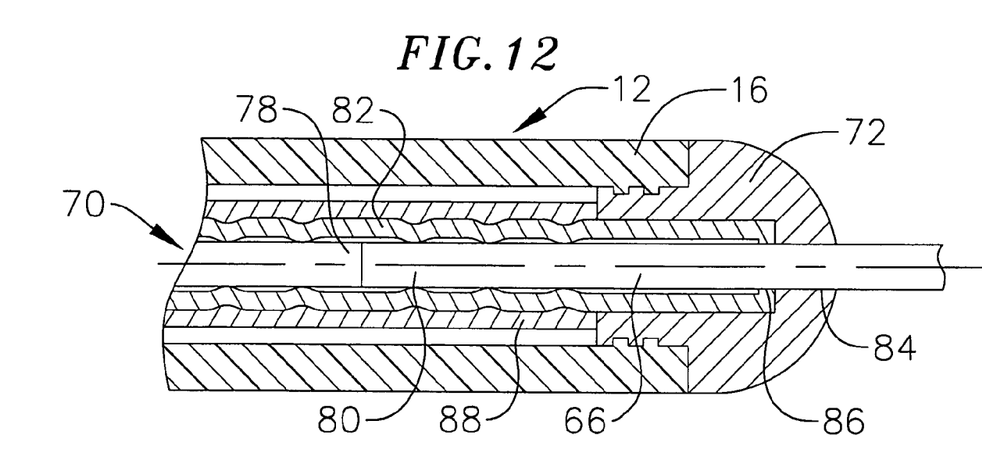
FIG. 12 is a partial section view of the tip region of the probe illustrated in FIG. 1.
Figure 13:
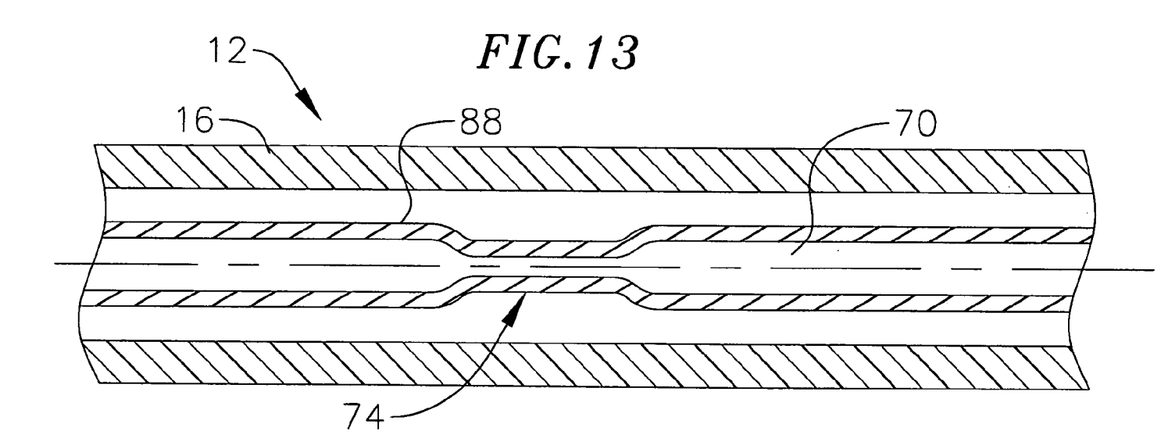
FIG. 13 is a partial section view of the hinge region of the probe illustrated in FIG. 1.

As illustrated in FIGS. 12 and 13, the exemplary catheter body 12 includes a flexible spline (or "core wire") 70. The flexible spline 70 is preferably a wire having a diameter of approximately 0.023 inch that is positioned inside of and passes within the length of the catheter body 12. The flexible spline 70 is fixedly secured to the handle 18 at the proximal end of the catheter body 12 and to a tip member 72 in the manner described below. The tip member 72 is in turn secured to the distal end of the catheter body 12 with adhesive. In the preferred embodiment, the flexible spline 70 is made from resilient, inert wire, such as Nitinol® material or 17-7 stainless steel. Resilient injection molded plastic can also be used. The exemplary spline 70 is round in cross section, although other cross sectional configurations can be used. The flexible spline 70 may, if desired, also have a preset curvature accomplished by thermally presetting the spline at 500° C. for 8 minutes. The super-elastic properties of the material should, however, be maintained.

The flexible spline 70 includes a flattened portion 74 that is located within the portion of the distal member 16 that forms the apex 76 of the loop 62. The flattened portion 74 acts as a hinge and allows the portion of the catheter body 12 distal to the flattened portion to be bent back into a loop with less force than would otherwise be required. The flattened portion 74 also causes the distal member 16 to bend, and the loop 62 to be formed, in a flat loop plane. The placement of the flattened portion 74 in the area that will form the apex 76 of the loop 62 also results in a much sharper bend at the apex, and a more compact loop, than would be obtained otherwise. Specifically, conventional loops often have a flattened portion near the proximal end of the loop and tend to assume a generally circular shape when deployed, while the present loop 62 in the exemplary embodiment has a generally flat, elliptical shape resulting from the location of the flattened portion 74.

The flattened portion 74 should also be thinner than the flattened portion in a conventional loop catheter. In an embodiment where the flexible spline 70 has a diameter of approximately 0.023 inch, the thickness of the flattened portion 74 would be about 0.008 inch, as compared to about 0.018 inch in a conventional catheter. It should be noted, however, the flattened portion should be heat treated at least three times during the flattening process in order to insure the requisite strength. The length of the exemplary flattened portion 74 is about 1.0 inch, but may range from 0.5 inch to 2.0 inches.

Figure 16A:
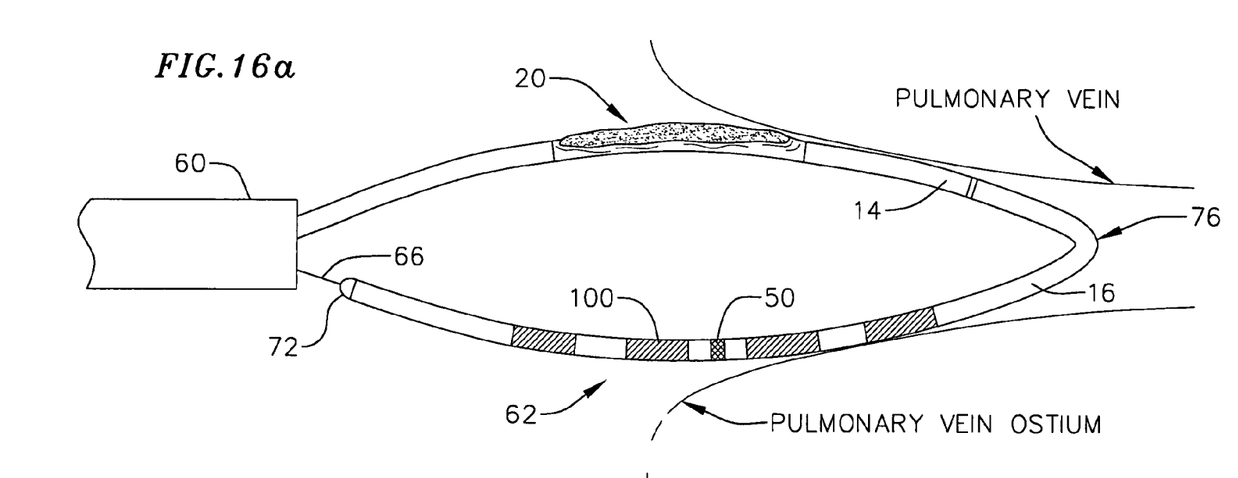
FIG. 16a is a side view showing the probe illustrated in FIG. 1 positioned adjacent the pulmonary vein ostium with the expandable electrode in a collapsed state.
Figure 16B:
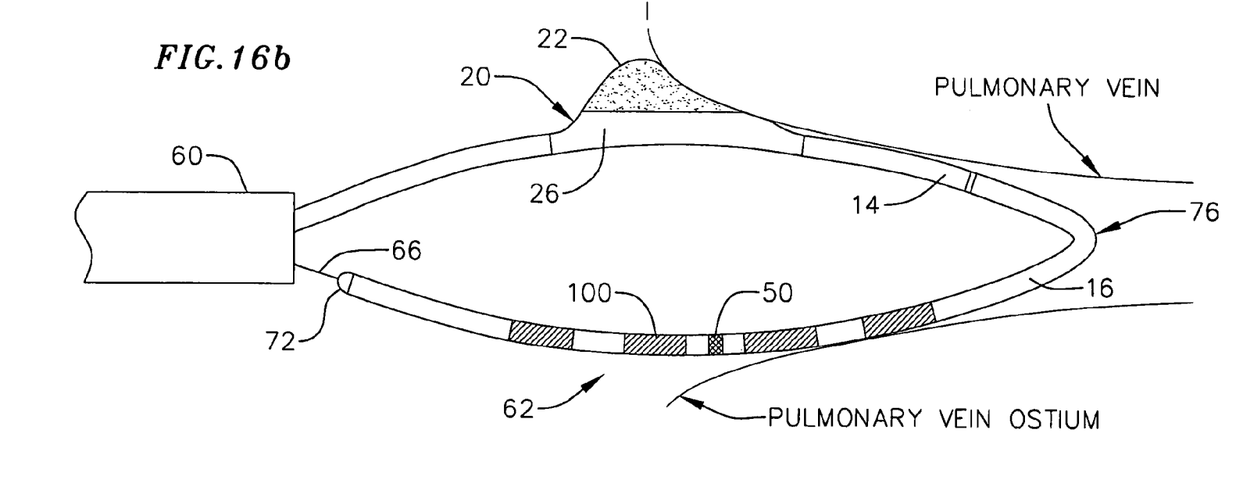
FIG. 16b is a side view showing the probe illustrated in FIG. 1 positioned adjacent the pulmonary vein ostium with the expandable electrode in an expanded state.

Preferably, the materials and configurations selected for the catheter body proximal member 14 and distal member 16, as well as the and the spline 70 and flattened portion 74, will produce a relatively flat elliptical loop 62 that can be inserted into a pulmonary vein in the manner illustrated in FIGS. 16a and 16b. In a preferred embodiment, the length (measured along the longitudinal axis of the catheter 10) will be about 3.0 cm, but may range from 2.0 cm to 4 cm, while the height (measured transverse to the longitudinal axis) will be about 20 mm, but may range from 15 mm to 30 mm.

It should also be noted that, in the exemplary embodiment, the intersection of the proximal and distal members 14 and 16 is located proximal of the flattened portion 74. This configuration provides at least two advantages. For example, locating the porous electrode 20 on the less flexible proximal member 14 (which also has better torque transmission properties) makes it easier to position the electrode during lesion formation procedures. Additionally, locating the flattened portion 74 within the relatively flexible distal member 16 improves bending at the apex 76 and makes it easier to pull the loop 62 into a compact orientation.

The flexible spline 70 may also be used to anchor the pull wire 66. As illustrated for example in FIG. 12, the distal end 78 of the flexible spline 70 is fixedly engaged in an in-line manner to the end 80 of the pull wire 66 with a stainless steel crimp tube 82. The in-line connection of the flexible spline 70 and pull wire 66 allows for a reduction in the overall diameter of distal portion of the catheter body 12. This provides a significant clinical advantage over devices having side by side pull wire connections which create a larger diameter device. The pull wire 66 passes through a pull wire bore 84 in the catheter tip member 72 and through a bore 86 in the distal end of the crimp tube 82.

The tip member 72 is preferably formed from platinum and is fixedly engaged with, for example, silver solder, adhesive or spot welding, to the distal end of crimp tube 82. The flexible spline 70 is preferably electrically insulated with a thin walled polyester heat shrink tube 88 that extends beyond the proximal end of the crimp tube 82. Other pull wire configurations, other methods of attaching the pull wire to the catheter body, and methods of reducing stress on the pull wire are disclosed in U.S. Pat. No. 6,048,329, which is incorporated herein by reference.

Figure 14:
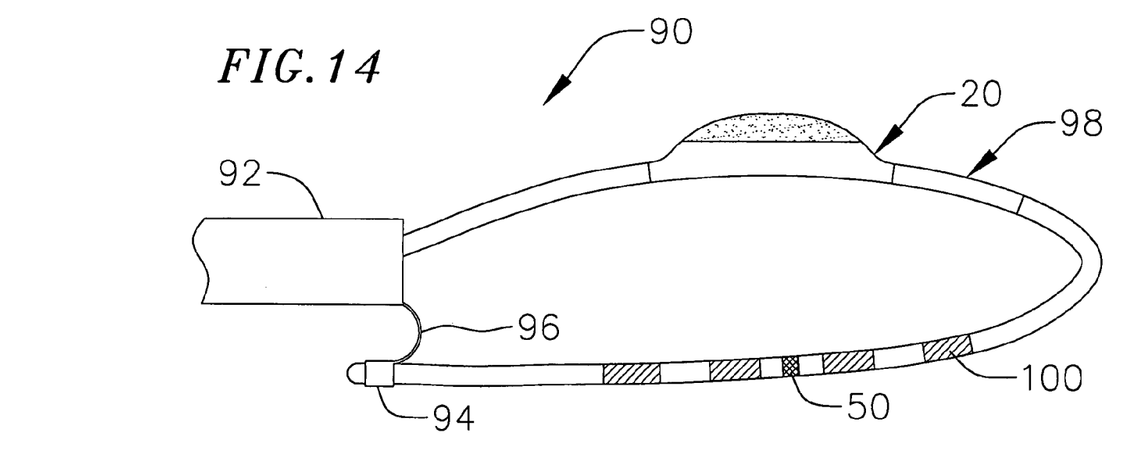
FIG. 14 is a side view of the distal portion of a catheter-based probe in accordance with another preferred embodiment of a present invention.

It should be noted that the present inventions are also applicable to loop catheters in which the distal portion of catheter body is connected to the distal portion of the sheath. As illustrated for example in FIG. 14, the exemplary catheter 90, which is otherwise identical to catheter 10, does not include a pull wire and instead is used in combination with a sheath 92 which has a distal member 94 that is connected to the distal end of the catheter 90. A slot is formed in the distal portion of the sheath 92 and the remnant 96 forms a flexible joint. The loop 98 is formed when the catheter 90 is urged distally relative to the sheath 92, thereby causing the distal portion of the catheter to bulge outwardly in the manner illustrated in FIG. 14. Other loop catheters where the distal portion of catheter body is connected to the distal portion of the sheath may also be used. One example is a catheter wherein the distal end of the catheter body is connected to the distal end of a sheath by a short wire. This and other examples of such loop catheters are disclosed in U.S. Pat. No. 6,071,274, which is incorporated herein by reference.

Figure 15:
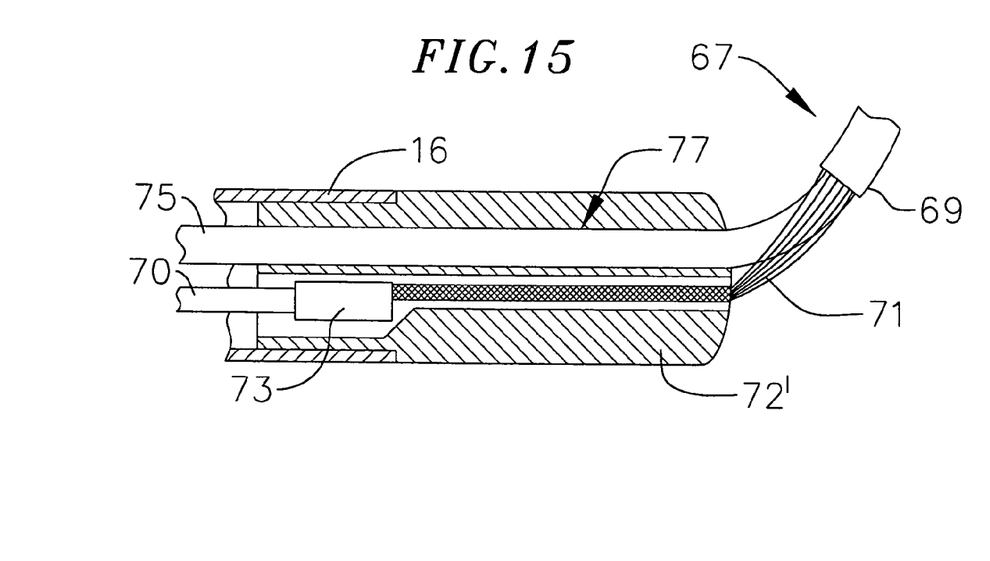
FIG. 15 is a side view of the tip region of a catheter-based probe in accordance with yet another preferred embodiment of a present invention.

As illustrated for example in FIG. 15, an infusion/ventilation pull device 67 may be used in place of the pull wire 66. The infusion/ventilation pull device 67 is especially useful in those instanced where a porous electrode 20 or coagulation body 58 is located distal of the apex 76 (such as in the exemplary embodiment illustrated in FIG. 9). Nevertheless, the infusion/ventilation pull device 67 may be used in conjunction with any of the embodiments described herein. The infusion/ventilation pull device 67 is preferably formed from a dual lumen braid tube with the outer portion 69 removed in the vicinity of the tip member 72' to expose the braids 71. One lumen is used for infusion and the other is used for ventilation. Alternatively, a braid tube with the braids on the exterior may be used.

In either case, the braids 71 are separated from the remainder of the tube and connected to the core wire 70 with a crimp tube 73. The inner portion 75 of the braid tube extends through an aperture 77 in the tip member 72' to the porous electrode 20 or coagulation body 58, where the ends of the dual fluid lumens are plugged. Apertures are formed through the wall of the inner portion 75 to each of the two lumens at positions within the porous electrode 20 or coagulation body 58. So configured, the infusion/ventilation pull device 67 may be used to perform the pull wire function in a loop catheter (or probe) in addition to the infusion/ventilation function.

IV. Methods of Use

The exemplary catheter 10 may be used to, for example, form a lesion around a pulmonary vein ostium in the following manner. With the expandable porous electrode 20 in a collapsed state, the sheath 60 and catheter 10 are directed into the left atrium and the loop 62 is then deployed in the manner described above. The loop 62 is compact enough to allow the apex 76 to be wedged into the pulmonary vein in the manner illustrated in FIG. 16a. This places core wire 70 in a compressed state and, accordingly, the upper and lower portions of the loop 62 (as oriented in FIG. 16a) push against the corresponding portions of the pulmonary vein ostium.

Next, conductive fluid is supplied to the expandable porous electrode 20 to expand the electrode into the state illustrated in FIG. 16b. The porous electrode 20 will press against, and conform to, the pulmonary vein ostium. The underlying loop 62 will also be acting as a brace to press the now expanded porous electrode 20 against the ostium. As a result, the porous electrode 20 will achieve the level of contact necessary to form an effective lesion.

With the porous electrode 20 urged against the pulmonary vein ostium, power is supplied to the electrode 46 to create a lesion. Once a lesion is created, the liquid will be removed from the porous electrode 20 to return it to its collapsed state. This allows the loop 62 to be rotated by the physician by, for example, rotating the handle 18. The loop 62 may have to also be withdrawn slightly prior to rotation. The porous electrode 20 will be re-expanded, and a lesion created, when the porous electrode is aligned with the next intended lesion location. This process will continue until a continuous lesion has been formed all the way around the pulmonary vein ostium.

After the formation of a lesion around the pulmonary vein is complete, a series of electrodes 100 positioned on the side of the loop 62 opposite the porous electrode structure 20 may be used for pacing and recording purposes to determine whether or not a continuous line of electrical block has been formed through conventional mapping techniques. The electrodes 100, which are connected to the connector 52 (FIG. 1) by conductors 102 (FIGS. 6, 7, 10 and 11), are preferably in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes are also about 4 mm in length. Other types of electrodes, such as wound spiral coils, helical ribbons, and conductive ink compounds that are pad printed onto a non-conductive tubular body, may also be used.

Although the present inventions have been described in terms of the preferred embodiments above, numerous modifications and/or additions to the above-described preferred embodiments would be readily apparent to one skilled in the art. By way of example, but not limitation, although the inflatable lesion formation is positioned on the proximal side of the flattened portion prior to formation of the loop, it may be positioned on the distal side if so desired. It is intended that the scope of the present inventions extend to all such modifications and/or additions and that the scope of the present inventions is limited solely by the claims set forth below.

We claim:

1. A probe for use with an outer member having a wall defining an interior bore, the probe comprising:
    an elongate body, defining a distal region, a distal end and a proximal region, adapted to be carried within the outer member interior bore, the distal region of the elongate body including a hinge portion that is more flexible than portions of the elongate body immediately proximal to the hinge portion and immediately distal of the hinge portion;
    an inflatable tissue coagulation body supported on the elongate body distal region; and
    a control element defining a distal portion fixedly secured to the elongate body and associated with the distal end of the elongate body and a proximal portion extending along the exterior of the elongate body toward the proximal region of the elongate body.

2. A probe as claimed in claim 1, wherein the elongate body comprises a catheter body.

3. A probe as claimed in claim 1, wherein at least the distal region of the elongate body includes a flexible spline.

4. A probe as claimed in claim 3, wherein the flexible spline includes the hinge portion.

5. A probe as claimed in claim 4, wherein the inflatable tissue coagulation body is proximal to the hinge portion.

6. A probe as claimed in claim 4, further comprising:
    at least one sensing element;
    wherein the inflatable tissue coagulation body is located one of distal of and proximal to the hinge portion and the at least one sensing element is located the other of distal of and proximal to the hinge portion.

7. A probe as claimed in claim 1, wherein the inflatable tissue coagulation body comprises a half-balloon structure.

8. A probe as claimed in claim 1, wherein the inflatable tissue coagulation body includes micropores.

9. A probe as claimed in claim 1, wherein the inflatable tissue coagulation body comprises a heated structure.

10. A probe as claimed in claim 1, wherein the control element comprises a pull wire.

11. A probe for use with an outer member having a wall defining an interior bore, the probe comprising:
    an elongate body, defining a distal region with a hinge portion, a distal end and a proximal region, adapted to be carried within the outer member interior bore;
    an inflatable tissue coagulation body supported on the elongate body distal region and located one of distal of and proximal to the hinge portion;
    at least one sensing element located the other of distal of and proximal to the hinge portion; and
    a control element defining a distal portion associated with the distal end of the elongate body and a proximal portion extending along the exterior of the elongate body toward the proximal region of the elongate body.

12. A probe as claimed in claim 11, wherein the elongate body comprises a catheter body.

13. A probe as claimed in claim 11, wherein at least the distal region of the elongate body includes a flexible spline and the flexible spline includes the hinge portion.

14. A probe as claimed in claim 11, wherein the inflatable tissue coagulation body includes micropores.

15. A probe as claimed in claim 11, wherein the inflatable tissue coagulation body comprises a heated structure.

16. A probe as claimed in claim 11, wherein the control element comprises a pull wire.

17. A probe for use with an outer member having a wall defining an interior bore, the probe comprising:
    an elongate body, defining a distal region, a distal end and a proximal region, adapted to be carried within the outer member interior bore;
    an inflatable half-balloon tissue coagulation structure supported on the elongate body distal region and configured to expand in some radial directions relative to the elongate body and to not expand in other radial directions relative to the elongate body; and
    a control element defining a distal portion associated with the distal end of the elongate body and a proximal portion extending along the exterior of the elongate body toward the proximal region of the elongate body.

18. A probe as claimed in claim 17, wherein the elongate body comprises a catheter body.

19. A probe as claimed in claim 17, wherein the inflatable half-balloon tissue coagulation body includes micropores.

20. A probe as claimed in claim 17, wherein the inflatable half-balloon tissue coagulation body comprises a heated structure.

21. A probe as claimed in claim 17, wherein the control element comprises a pull wire.

* * * * *